US006158439A

United States Patent [19]

Streetman

[11] Patent Number: 6,158,439

[45] Date of Patent: Dec. 12, 2000

[54] METHOD AND DEVICE FOR TREATING HEADACHES, SINUS CONGESTION AND CONGESTION AS WELL AS DRUG WITHDRAWAL

[76] Inventor: Foy Streetman, 401 Chickasha Ave., Chickasha, Okla. 73023

[21] Appl. No.: 09/337,076

[22] Filed: Jun. 21, 1999

[51] Int. Cl.[7] ..................... A61B 19/00

[52] U.S. Cl. ..................... 128/898; 601/46

[58] Field of Search ..................... 128/898, 857, 128/859, 861; 601/2, 46, 139; 482/10, 11

[56] References Cited

U.S. PATENT DOCUMENTS

| | | | |
|---|---|---|---|
| 761,029 | 5/1904 | Brown . | |
| 947,251 | 1/1910 | Muller . | |
| 1,466,559 | 8/1923 | Purdy . | |
| 1,586,499 | 5/1926 | Worth . | |
| 1,749,632 | 3/1930 | Ferris . | |
| 2,021,445 | 11/1935 | Engstrom | 128/25 |
| 4,700,695 | 10/1987 | Davis . | |
| 5,421,799 | 6/1995 | Rabin . | |

*Primary Examiner*—Dinh X. Nguyen
*Attorney, Agent, or Firm*—R. William Graham

[57] ABSTRACT

A vibrational instrument which is therapeutically beneficial in treating the person suffering from afflictions such as headache, sinus congestion and pressure, and withdrawal due to drug dependency includes a member capable of transmitting vibrational waves through the teeth, jaw and sinus tissue for disposal between teeth of the person. A method of treatment is also provided.

9 Claims, 2 Drawing Sheets

METHOD AND DEVICE FOR TREATING HEADACHES, SINUS CONGESTION AND CONGESTION AS WELL AS DRUG WITHDRAWAL

BACKGROUND OF THE INVENTION

1. Field of Invention

This invention relates to the field of therapeutic treatment of headaches and sinus related ailments, such as headaches, congestion and pressure as well as withdrawal due to drug dependency. The invention provides a method and device which are found to be very useful in treating and relieving one suffering from a headache, sinus congestion and pressure as well as withdrawal due to drug dependency by way of vibrational therapy.

2. Related Art

Presently, there exist many of treatments for sinus headaches, sinus congestion and pressure as well as withdrawal due to drug dependency. Many of these treatments utilize drugs such as conventional analgesics, (an aspirin or low dosage of an addict drug, e.g., nicotine). While medicinal remedies have proven effective, they are required to be taken internally and is consequently a drug which is less desirable than natural or holistic approaches to treating such ailments.

Millions of persons seek medical help for headaches due to sinus problems and billions of dollars are spent on headache remedies annually. There exist many treatments for headaches. For example, the Chinese used acupuncture to relieve head pain. The ancient Greeks and Romans used cathartics and bloodletting to treat headaches. The pre-Columbian Incas of Peru drilled holes in the skull to release the evil spirits that they believed to be at the root of the problem. Today a headache is mostly treated with a wide variety of drugs and behavior modification techniques.

Headache pain results from the stimulation of such pain-sensitive structures as the membranous linings of the brain (the meninges) and the nerves of the cranium and upper neck. This stimulation can be produced by inflammation, by the dilation of blood vessels of the head, or by sustained muscle contractions in the neck and head. Headaches brought on by muscle spasms are classified as tension-type headaches; those caused by the dilation of blood vessels are called vascular headaches. A more specialized classification, by the International Headache Society, further divides headaches into 14 categories for research purposes.

A small percent of all headaches result from organic disorders, including diseases of the eye, ear, nose, throat, and sinuses; brain tumors; and aneurism (the ballooning of an artery, brought about by a weakness in the arterial wall). The most common form of a headache is the tension-type headache, which can be divided into two categories—episodic and chronic. People rarely visit physicians because of tension headaches.

Sinus cavities within the head are mucus-lined air cavities in facial bones and certain blood passageways. In humans, sinuses surround the nose and referred to as the paranasal sinuses. They extend from the nasal cavities into adjoining bones and are connected to the nose by passageways. The bones that contain sinuses are the frontal, sphenoid, ethmoid, and maxillary bones.

Vascular headaches are probably the most severe form and are the most frequent reason cited for patients visiting a physician with the primary complaint of a headache. Vascular headaches include migraine, cluster, and hypertensive headaches. Chronic sinus problems rarely cause headaches, although these are frequently cited in the media as a major headache trigger. Acute sinusitis, with an accompanying fever, can precipitate a headache, and the underlying infection must be treated to relieve the symptom.

Tension-type headaches can be subdivided into episodic and chronic. Episodic is recurrent and mild and commonly relieved by over-the-counter analgesics. Chronic forms may continue for many years and do not respond to simple analgesics. Chronic tension-type headaches may be due to inherent anxiety or depression. Patients with chronic daily headaches have an increased potential for habituation to analgesics, whether prescription or over-the-counter. Some of these cases have to be treated through psychotherapy.

The two most common types of a vascular headache are migraine and cluster headaches for which there is no known cure. Migraine therapy can be divided into four categories: general measures, abortive therapy, prophylactic therapy, and pain relief. General measures include identifying and avoiding triggers (such as the food items listed previously), relaxation techniques, and biofeedback. A variety of drugs are used to diminish or eliminate the migraine including ergot preparations, isometheptene mucate, nonsteroidal anti-inflammatory drugs (NSAIDS) and Dihydroergotamine (DHE), a derivative of ergotamine. Research has implicated the neurotransmitter called serotonin in the development of migraine.

Cluster headaches known as migrainous neuralgia, Horton's histamine headache, and erythromelalgia of the head, produce short, severe attacks of pain centered over one eye. It is suspected that cluster headaches may be caused by a disorder in histamine metabolism, since they are usually accompanied by allergy symptoms such as tearing, nasal congestion, and a runny nose.

Still, with all the treatments available, there is a need for a more holistic non drug approach which is also effective and relatively low cost. The present invention provides such a treatment.

SUMMARY OF THE INVENTION

It is an object to treat one suffering from sinus related afflictions.

It is another object to therapeutically treat sinus related ailments using vibrational therapy.

It is another object to provide an article of manufacture which is useful in treating sinus related ailments.

It is still another object to treat withdrawal due to drug dependency.

Accordingly, the present invention in one sense is directed to a method of treating a person suffering from headache, sinus congestion and pressure or withdrawal due to drug dependency. The method includes the steps of placing an instrument inside a person's mouth, wherein the instrument is capable of propagating a vibrational wave therethrough in a manner to have a therapeutically beneficial effect by relieving the patient's ailment when disposed between maxilla and mandible teeth, and actuating the instrument in a manner to cause vibrational waves to propagate there through. In this way, the vibrational waves propagate through the teeth, jaw bones of the person and connecting sinus tissue. This is found to be therapeutically beneficial for treating the aforesaid afflictions.

In another sense, the invention provides for a vibrational instrument which is therapeutically beneficial in treating the person suffering from the recited afflictions. A preferred embodiment is directed to an elongated bendable member having a first end for disposal between teeth of the person, and a second end which extends sufficiently from the first end to be externally positioned outside of the mouth when the first end is disposed between the teeth. The instrument is further characterized to be of a material which when held between the teeth at the first end and caused to bend by applying a force on the second end, thus bending the member, and releasing the second end results in vibrational waves propagating through the teeth, jaw and sinus tissue as described to provide a therapeutic effect.

The member can be of a plastic and configured to provide enhanced vibration. While Simplistic in the design set forth, it is contemplated that sophisticated means of carrying out the present invention can be obtained with mechanical and/or electrical means. In another embodiment, there is provided a vibrational instrument which is therapeutically beneficial in treating the person suffering from headache, sinus congestion and pressure, and withdrawal due to drug dependency, which includes a member capable of transmitting vibrational energy waves and for disposal between teeth of the person, and means operably connected to said member for causing vibrational energy waves to propagate through the teeth, jaws, sinus tissue and head to provide a therapeutic effect.

DETAIL DESCRIPTION OF THE PREFERRED EMBODIMENTS

Figure 1:
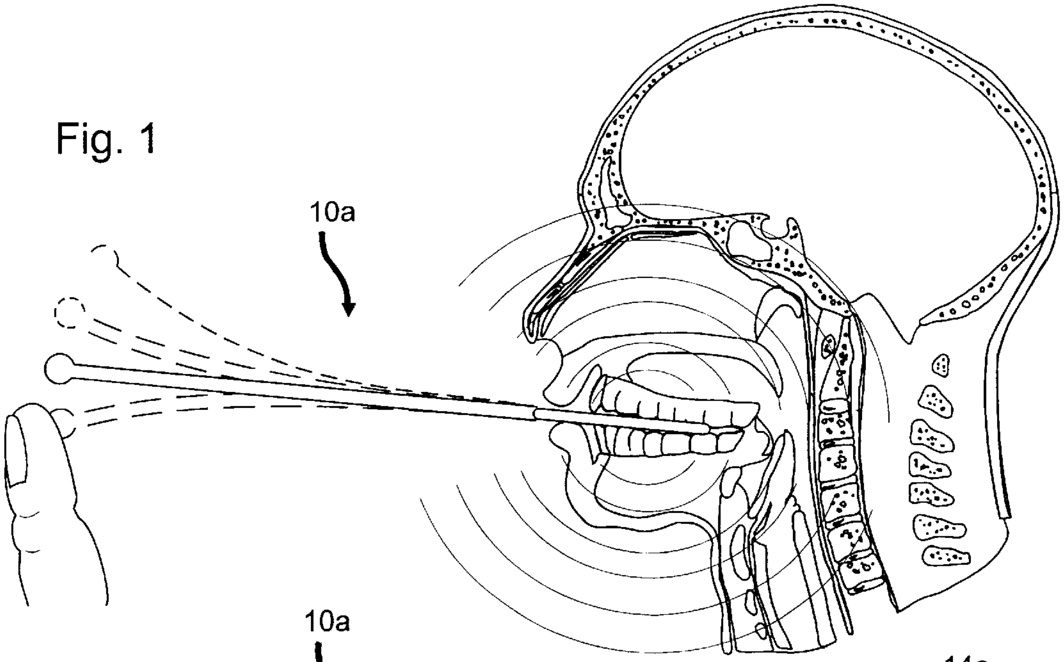
FIG. 1 illustrates the use of an embodiment of the present invention in use.
Figure 2:
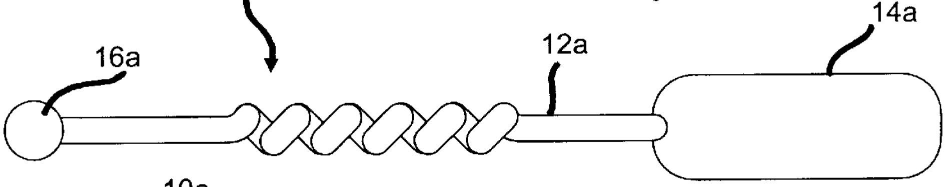
FIG. 2 is a plan view of the embodiment of the present invention.
Figure 2A:
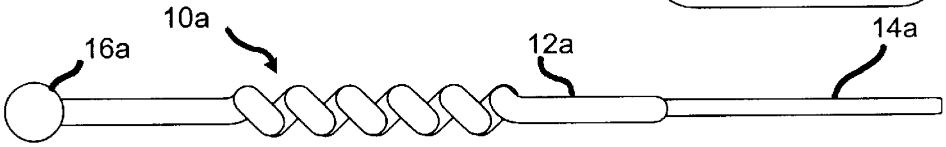
FIG. 2A is a side view of the embodiment of the present invention.
Figure 3:
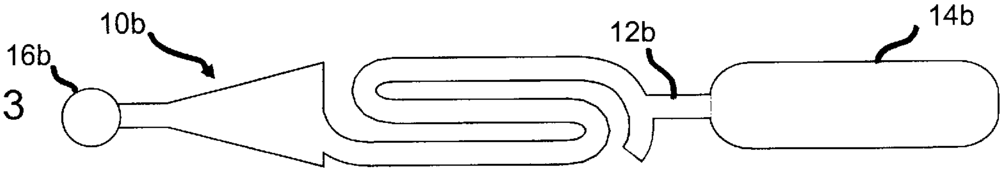
FIG. 3 is a plan view of another embodiment of the present invention.
Figure 3A:
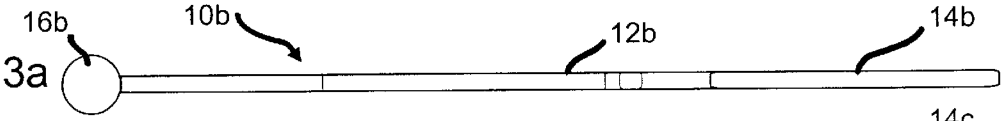
FIG. 3A is a side view of the embodiment of the present invention.
Figure 4:
FIG. 4 is a plan view of still another embodiment of the present invention.
Figure 4A:
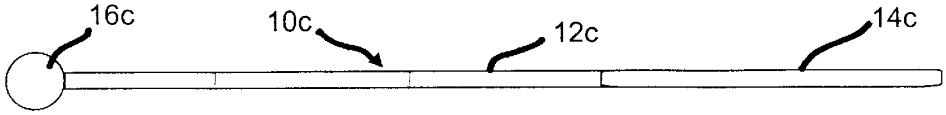
FIG. 4A is a side view of the embodiment of the present invention.

Referring to the drawings, the present invention is generally referred to by the numerals 10A, 10B, 10C, and 10D. FIGS. 1, 2 and 2A depict the embodiment 10A, whereas FIGS. 3, 3A and 4, 4A show variations of the embodiment in FIG. 2 which are similar in function. Accordingly, the instrument 10A will be described with the understanding that corresponding description like elements for instruments' 10B and 10C.

The instrument 10A is a vibrational instrument which is therapeutically beneficial in treating a person suffering from the recited afflictions. The instrument 10A includes an elongated bendable member 12A having a first end 14A for disposal between teeth of the person as shown in FIG. 1, and a second end 16A which extends sufficiently from the first end 14A to be externally positioned outside of the person's mouth when the first end 14A is disposed between the teeth. The instrument 10A is further characterized to be of a material which when held between the teeth at the first end 14A and caused to bend by applying a force on the second end 16A, thus bending the member, and releasing the second end 16A results in vibrational waves propagating through the teeth, jaw and sinus tissue as described to provide a therapeutic effect.

The first end 14A is shown as relatively planar and is generally of a width that of the posterior teeth to be held proximate the maxillary and mandible jaw bones. The second end 16A is preferably a thinner width, although could be the same or larger than that of the first end 14A, and extends out of the mouth. The ends 14A and 16A are preferably integrally formed. The second end 16A can be configured with a number of different shapes which are preferably designed to optimally transmit vibrational energy through the instrument 10A, to the maxillary and mandible jaws and ultimately to the sinus and head to relieve the affliction. For example, the end 16A can be formed with a number of bends as depicted in the drawings to increase bendability. In carrying out the method for using this embodiment, the person suffering from one of the above afflictions, simply places the end 14A between maxilla and mandible teeth in a firm bite. Then, the end 16A is bent to a sufficient degree and released where upon such release, there is vibrational wave energy transmitted through the member 12A, teeth, jaws, sinus tissue and head. This activity is repeated as required by the person to provide the therapy as needed.

Figure 5:
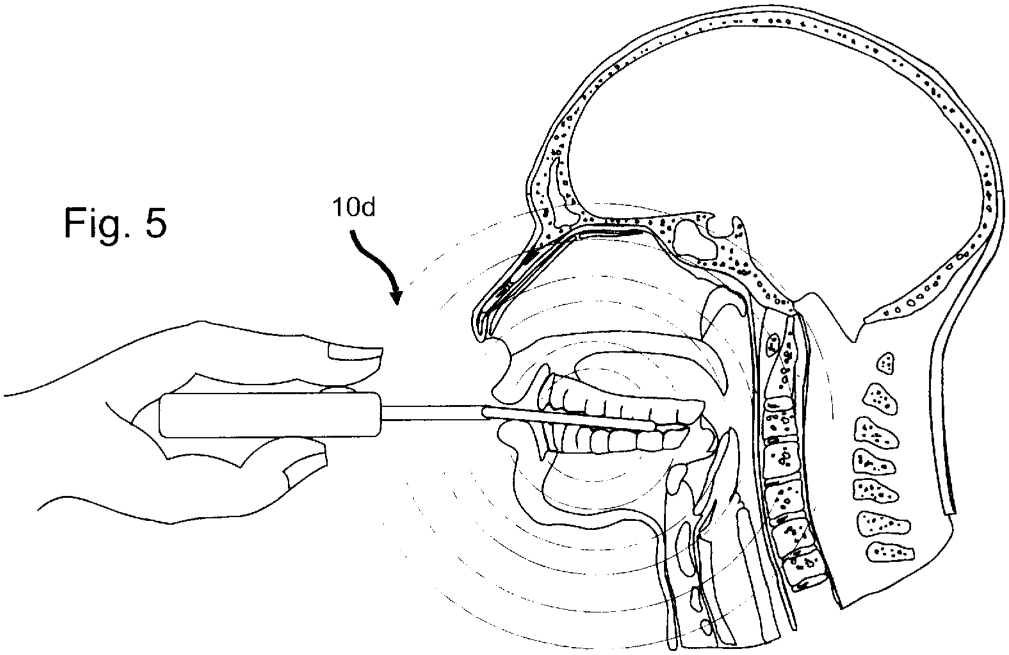
FIG. 5 is a view of another embodiment of the present invention in use.
Figure 6:
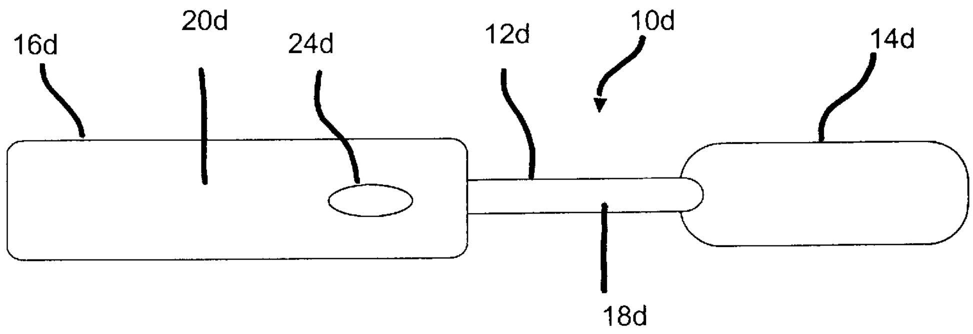
FIG. 6 is a plan view of the embodiment of the FIG. 5.
Figure 7:
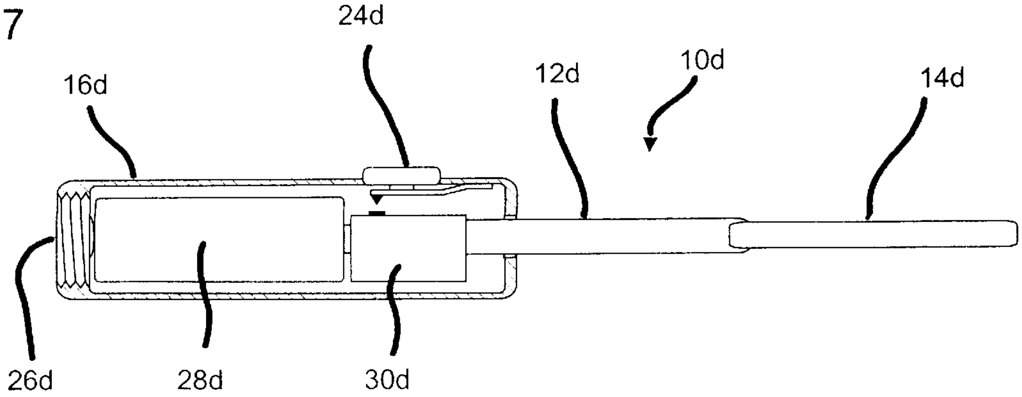
FIG. 7 is a cross-sectional view of the embodiment of FIG. 5.

Alternatively, another instrument 10D embodiment is shown in FIGS. 5–6 is provided. Here, the instrument 10D is automated and includes a member 12D having a first end 14D which is formed in a manner not unlike that of end 14A described above. The second end 16D includes a portion 18D connected to the first end 14D and another housing portion 20D which houses vibrating apparatus 22D. A switch 24D is operably disposed on the housing portion 20D. The housing portion 20D includes a removable panel 26D through which a battery 28D may be passed, wherein the battery 28D is operably disposed within the housing portion 20D. A small electrical motor 30D is operably disposed within the housing portion 20D and includes an off-center weight mechanism (not shown). As the motor 30D is driven, a vibrational wave energy is passed through the member 12D, end 14D and into the teeth, maxillary and mandible jaw bones, sinus cavities and head. The method of use for this embodiment simply requires the person to place the end 14D between the teeth as previously described. Here, one simply actuates the switch 24D and therapy continues for as long as is desired.

The member can be of a plastic and configured to provide enhanced vibration. While Simplistic in the design set forth, it is contemplated that sophisticated means of carrying out the present invention can be obtained with other mechanical and/or electrical means which will be readily apparent to those skilled in the art. Accordingly, the above embodiments are exemplary and the claims appended hereto include such modifications, derivatives and improvements of the present invention which are obvious to a person skilled in the art.

What is claimed is:

1. A method of providing therapy to a person suffering from headache pain resulting from sinus congestion and pressure, or withdrawal due to drug dependency, including the steps of:

(a) placing an instrument inside a person's mouth such that said instrument is capable of propagating a vibrational wave therethrough in a manner to have a therapeutically beneficial effect when disposed in a bite between maxilla and mandible teeth; and (b) actuating the instrument in a manner to cause vibrational energy waves to propagate therethrough to provide a therapeutic effect.

2. The method of claim 1, wherein the step (b) includes means for automatically causing vibrational energy waves.

3. The method of claim 1, wherein the step (b) includes means for manually causing vibrational energy waves.

4. A method of providing therapy to a person suffering from headache pain resulting from sinus congestion and pressure or withdrawl due to drug dependency, including the steps of:

(a) placing an instrument inside a person's mouth wherein said person bites on said instrument, said instrument being capable of propagating a vibrational wave therethrough in a manner to have a therapeutically effective effect; and (b) causing vibrational energy waves to propagate through said instrument to provide a therapeutic effect.

5. The method of claim 4, which further characterizes the step of biting to occur between maxilla and mandible teeth.

6. The method of claim 4, wherein the step (b) to include means for automatically causing vibrational energy waves.

7. The method of claim 1, wherein the step (b) includes means for manually causing vibrational energy waves.

8. The method of claim 2 wherein said means for automatically causing vibrational energy waves includes mechanical and/or electrical means.

9. The method of claim 6 wherein said means for automatically causing vibrational energy waves includes mechanical and/or electrical means.

* * * * *